(12) United States Patent
Uesugi et al.

(10) Patent No.: US 7,863,412 B2
(45) Date of Patent: Jan. 4, 2011

(54) METHOD FOR MIXING OBJECT INTO GELLED ASSEMBLY

(75) Inventors: Koji Uesugi, Aichi (JP); Yusuke Nagai, Aichi (JP); Hidenori Yokoi, Aichi (JP)

(73) Assignee: Menicon Co., Ltd., Aichi (JP)

( * ) Notice: Subject to any disclaimer, the term of this patent is extended or adjusted under 35 U.S.C. 154(b) by 0 days.

(21) Appl. No.: 12/705,914

(22) Filed: Feb. 15, 2010

(65) Prior Publication Data

US 2010/0227398 A1    Sep. 9, 2010

(30) Foreign Application Priority Data

Mar. 9, 2009    (JP)    ............................. 2009-054982

(51) Int. Cl.
- *B01J 13/00* (2006.01)
- *B01J 19/06* (2006.01)
- *C07K 1/00* (2006.01)

(52) U.S. Cl. ................ 530/300; 366/144; 502/80; 516/98; 516/103; 530/427

(58) Field of Classification Search ............... None
See application file for complete search history.

(56) References Cited

U.S. PATENT DOCUMENTS

| 1,949,360 A * | 2/1934 | Schorger .................. 423/711 |
| 5,670,483 A | 9/1997 | Zhang et al. |
| 7,799,194 B2 * | 9/2010 | Makuska .................... 204/469 |
| 2002/0175440 A1 | 11/2002 | Bessho et al. |
| 2006/0211567 A1 | 9/2006 | Kuhn et al. |
| 2007/0197701 A1 * | 8/2007 | Kato et al. .................. 524/256 |
| 2008/0117713 A1 | 5/2008 | Bessho et al. |

FOREIGN PATENT DOCUMENTS

| JP | 62-115063 A | 5/1987 |
| JP | 05-068511 A | 3/1993 |
| JP | 2003-206181 A | 7/2003 |
| JP | 2007-217375 A | 8/2007 |
| JP | 2007-514629 A | 9/2007 |

OTHER PUBLICATIONS

Yokoi et al. (2005) "Dynamic Reassembly of Peptide RADA16 Nanofiber Scaffold" PNAS, 102(24)8414-8419.

* cited by examiner

*Primary Examiner*—Jeffrey E Russel
(74) *Attorney, Agent, or Firm*—Swanson & Bratschun, L.L.C.

(57) ABSTRACT

This invention provides a mixing method by which a mixing object can be uniformly mixed into a gelled assembly within a short time period. The method for mixing a mixing object into a gelled assembly comprises freezing the gelled assembly; melting the frozen assembly to obtain a sol; mixing the resultant sol and the mixing object; and reconstituting the gelled assembly from the sol into which the mixing object has been mixed.

5 Claims, 4 Drawing Sheets

METHOD FOR MIXING OBJECT INTO GELLED ASSEMBLY

RELATED APPLICATIONS

This application claims priority under 35 U.S.C. Section 119 to Japanese Patent Application No. 2009-054982 filed on Mar. 9, 2009, which is herein incorporated by reference.

BACKGROUND

1. Field of the Invention

The present invention relates to a method for mixing an object into a gelled assembly.

2. Description of the Related Art

Gelled assemblies have been attracting attention in recent years. Of those, a gelled assembly formed by the molecular-assembling of molecules each having self-assembling ability has been attracting particular attention, and has been expected to find use in various applications. Such gelled assembly is, for example, a peptide gel as a molecular-assembly of a self-assembling peptide, and the peptide gel has been applied to a cell-scaffold in the field of, for example, regenerative medicine. When the peptide gel is used as the scaffold, upon mixing of the peptide gel that has already gelled and an object such as a cell, a method involving subjecting the gel to an ultrasonic treatment for about 30 minutes and mixing the resultant and the object has been adopted (Proc Natl Acad Sci USA, 2005, 102 (24) 8414-8419). However, the method involves such problems that the ultrasonic treatment requires much time and effort, and further, the object is not sufficiently dispersed.

SUMMARY

The present invention has been made with a view to solving the above problems, and a purpose of the present invention is to provide a mixing method by which a mixing object can be uniformly mixed (for example, dispersed) in a gelled assembly within a short time period.

According to one aspect of the invention, a method for mixing a mixing object into a gelled assembly is provided. The method includes:

freezing the gelled assembly;
melting the frozen assembly to obtain a sol;
mixing the resultant sol and the mixing object; and
reconstituting the gelled assembly from the sol into which the mixing object has been mixed.

In one embodiment of the invention, the gelled assembly includes a gel formed by molecular-assembling of self-assembling molecules.

In one embodiment of the invention, the gelled assembly includes a gel formed by assembling of clay mineral crystals.

In one embodiment of the invention, the self-assembling molecules include self-assembling peptides.

According to another aspect of the invention, a method for producing a gelled assembly into which a mixing object has been mixed is provided. The method includes:

freezing the gelled assembly;
melting the frozen assembly to obtain a sol;
mixing the resultant sol and the mixing object; and
reconstituting the gelled assembly from the sol into which the mixing object has been mixed.

According to still another aspect of the invention, a gelled assembly into which a mixing object has been mixed is provided. The assembly is obtained by the above production method.

According to the present invention, the mixing object can be uniformly mixed (for example, dispersed) within a short time period because the mixing is performed in a state where the gelled assembly has been turned into a sol.

DETAILED DESCRIPTION

Figure 1B:
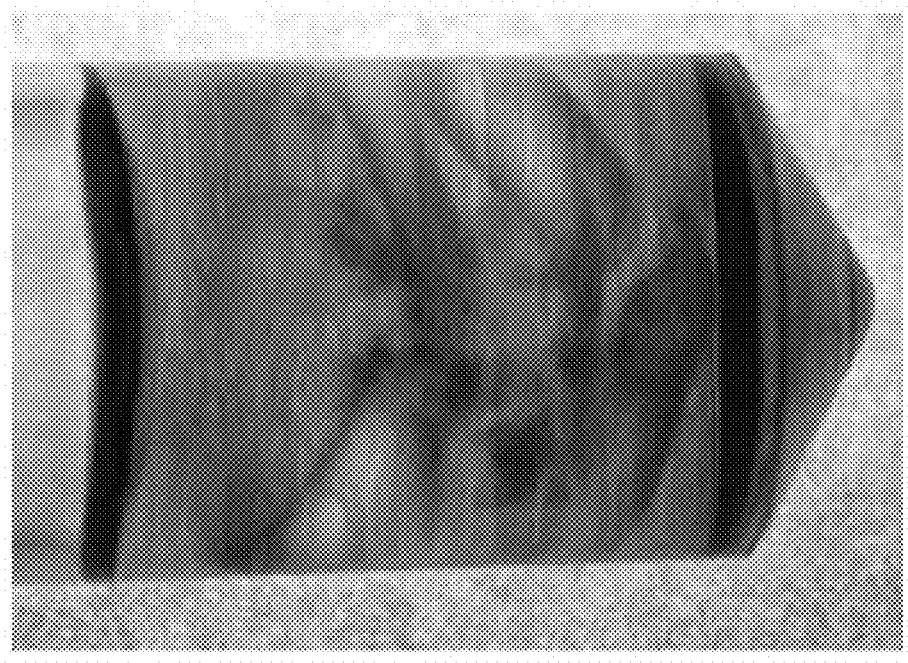
FIG. 1A is a photograph of a gel reconstituted in Example 1 and FIG. 1B is a photograph of a gel reconstituted in Comparative Example 1.

A. Definition of Terms (1) Gelled Assembly

The term "gelled assembly" refers to a gel formed by spontaneous assembling of self-assembling molecules or crystals each having self-assembling ability in a medium.

(2) Self-assembling Molecules

The term "self-assembling molecules" refers to molecules that spontaneously assemble in the medium through an interaction between them. Such molecules can spontaneously aggregate by an intermolecular attraction, thereby forming a molecular group in an orderly and stable fashion without recourse to any covalent bond (so-called molecular-assembling). The interaction is not particularly limited, and examples of the interaction include a hydrogen bond, an ion-ion interaction, an electrostatic interaction such as a van der Waals force, and a hydrophobic interaction.

(3) Gel

The term "gel" refers to a colloid that has lost its flowability. The gel has both viscous property and elastic property. To be specific, for example, the gel satisfies the relationship [$G'>G''$] when its storage elastic modulus $G'$ and loss elastic modulus $G''$ are measured by performing dynamic viscoelasticity measurement.

(4) Sol

The term "sol" refers to a colloid having flowability. To be specific, for example, the sol satisfies the relationship [$G'<G''$] when its storage elastic modulus $G'$ and loss elastic modulus $G''$ are measured by performing the dynamic viscoelasticity measurement.

(5) Sol-gel Transition

The term "sol-gel transition" refers to a phenomenon in which the storage elastic modulus $G'$ and the loss elastic modulus $G''$ undergo a transition from a state where the relationship [$G'>G''$] is satisfied to a state where the relationship [$G'<G''$] is satisfied or from a state where the relationship [$G'<G''$] is satisfied to a state where the relationship [$G'>G''$] is satisfied, and the temperature at which the phenomenon occurs is called a sol-gel transition point. That is, the sol-gel transition point is the temperature at which the relationship [$G'=G''$] is satisfied.

B. Mixing Method

A mixing method of the present invention is a method for mixing a mixing object into a gelled assembly, the method including:

freezing the gelled assembly (freezing step);
melting the frozen assembly to obtain a sol (melting step);

mixing the resultant sol and the mixing object (mixing step); and reconstituting the gelled assembly from the sol into which the mixing object has been mixed (gelling step). The method may further include any step as required. When the gelled assembly is a gel formed by the molecular-assembling of self-assembling molecules, intermolecular bonds are broken by the freezing and the melting steps, and hence a three-dimensional network structure forming the gel collapses. As a result, a sol in which the molecules are uniformly dispersed can be obtained. In addition, when the gelled assembly is a gel formed by the assembling of crystals each having self-assembling ability, intercrystalline bonds are broken by the freezing and the melting steps. As a result, a sol in which the crystals are uniformly dispersed can be obtained. In the present invention, the sol having high homogeneousness thus obtained and the mixing object are mixed, and hence the mixing object can be present in the reconstituted gelled assembly in a state of being uniformly dispersed. The fact that the mixing object can be uniformly dispersed in the gelled assembly through extremely simple operations, i.e., the freezing and the melting steps is one of the major effects of the present invention.

B-1. Freezing Step

Any appropriate assembly can be adopted as the gelled assembly as long as the assembly forms a sol by the freezing and the melting steps, and has a reversible sol-gel transition characteristic. The transition to the gel from the sol formed by the freezing and the melting steps may be attributable to any one of a time responsivity, a temperature responsivity, and a pressure responsivity, or may be attributable to two or more factors out of the above responsivities. The gelled assembly contains molecules or crystals for forming the assembly and a medium, and as required, any additive.

Any appropriate molecules or crystals can be selected as the self-assembling molecules or the crystals each having self-assembling ability described above as long as the molecules or the crystals form a colloid having a reversible sol-gel transition characteristic, and form a sol by the freezing and the melting steps. The self-assembling molecules are each preferably, for example, a self-assembling peptide. The crystals each having self-assembling ability are each preferably, for example, a clay mineral. The gel formation of such molecules or crystals does not use a gelling agent such as a crosslinking agent or an agglomerating agent, and depends on relatively weak non-covalent bonds formed between the self-assembling molecules or crystals. Accordingly, those bonds are easily broken by the freezing and the melting treatments, and hence the gel can be turned into a sol. In addition, reconstitution of the gel from the sol can be spontaneously performed by molecular-assembling.

The self-assembling peptide is preferably, for example, a self-assembling peptide formed of the following amino acid sequence.

Amino acid sequence: $a_1b_1c_1b_2a_2b_3db_4a_3b_5c_2b_6a_4$ (In the amino acid sequence:

$a_1$ to $a_4$ each represent a basic amino acid residue;

$b_1$ to $b_6$ each represent a non-charge polar amino acid residue and/or a hydrophobic amino acid residue, provided that at least five of them each represent a hydrophobic amino acid residue;

$c_1$ and $c_2$ each represent an acidic amino acid residue; and d represents a hydrophobic amino acid residue.)

Specific examples of the self-assembling peptide having the above amino acid sequence include peptides having the following sequences.

```
n-RLDLRLALRLDLR-c      (SEQ ID NO: 1)

n-RLDLRLLLRLDLR-c      (SEQ ID NO: 2)

n-RLDLRLALRLDLRL-c     (SEQ ID NO: 3)
```

Other preferred specific examples of the self-assembling peptide include peptides described in, for example, WO 2007/000979 and U.S. Pat. No. 5,670,483. In addition, a peptide obtained by subjecting any such self-assembling peptide to a modification such as the introduction of a protective group is also preferably applicable to the method of the present invention.

The above self-assembling peptide can be produced by a chemical synthesis method such as a solid phase method, e.g., an Fmoc method or a liquid phase method, or by a molecular biological method such as recombinant gene expression.

Preferred specific examples of the clay mineral include smectite group minerals such as montmorillonite, beidellite, hectorite, saponite, and stevensite. Those minerals may be natural products, or may be synthetic products.

The medium of the gelled assembly can be appropriately selected depending on, for example, the kinds and concentration of the molecules or crystals for forming the assembly. In the case of, for example, a gelled assembly formed of a self-assembling peptide or clay mineral, its medium is preferably water.

The above additive can be appropriately selected depending on, for example, the kinds and concentration of the molecules or crystals for forming the assembly. Examples of the additive include a buffering agent, a surfactant, and a chelating agent.

The concentration of the additive in the gelled assembly can be set to such a concentration that the reconstitution of the gel in the gelling step is not adversely affected. Although the concentration can be appropriately set depending on, for example, the kinds and concentration of the molecules or crystals for forming the gelled assembly, the concentration is preferably low in ordinary cases. In the case of, for example, a self-assembling peptide gel, the final concentration of each of HEPES and Tris-HCl as buffering agents is preferably 50 mM or less, or more preferably 40 mM or less, the final concentration of each of a sodium hydrogen carbonate solution and a sodium carbonate solution is preferably 5 mM or less, or more preferably 4 mM or less, and the final concentration of PBS is preferably 0.5×PBS or less, or more preferably 0.3×PBS or less. In addition, the final concentration of pharmacopoeial saline as an additive except the buffering agent is preferably 0.5 wt % or less, or more preferably 0.4 wt % or less.

The above gelled assembly can be prepared by any appropriate method depending on, for example, the kinds and concentration of the molecules or crystals for forming the assembly, and the kind of the medium. For example, the self-assembling peptide gel can be prepared by preparing a peptide sol through such dissolution or dispersion of a self-assembling peptide in a desired medium that the concentration of the peptide is preferably 0.1 to 5 w/v % or more preferably 0.2 to 3 w/v %, and leaving the peptide sol at rest to assemble the molecules of the self-assembling peptide. Alternatively, the self-assembling peptide gel is available as a commercial product under the trade name of, for example, "BD™ PuraMatrix™ Peptide Hydrogel" (BD Biosciences Inc.). In addition, the gelled assembly formed of the mineral clay is available as a commercial product under the trade name of, for example, "Laponite XLG" (manufactured by Laporte-Ind. Ltd.) or "Laponite RD" (manufactured by Laporte-Ind. Ltd.).

Any appropriate conditions can be adopted as conditions for the freezing as long as the gelled assembly freezes. A freezing temperature has only to be equal to or lower than the temperature at which the gelled assembly freezes. A freezing velocity is not limited either, and the gelled assembly may be gradually frozen, or may be rapidly frozen. In the case of, for example, the self-assembling peptide gel, the gel can be suitably frozen by being left under a temperature condition of preferably −10° C. or lower.

Any appropriate freezing means such as a household or business-use refrigerator, or liquid nitrogen can be selected as a freezing means. It should be noted that the frozen assembly can be stored while being frozen for any time period until the assembly is subjected to the melting step.

B-2. Melting Step

A melting temperature can be set to any appropriate temperature as long as the above frozen assembly melts at the temperature to form a sol. The assembly may be melted at a constant temperature, or may be melted at different temperatures in a stepwise fashion. Neither a melting velocity nor a melting time is limited, and the assembly may be gradually melted, or may be rapidly melted. For example, in the case where the sol of the self-assembling peptide is obtained, the frozen self-assembling peptide can be suitably melted by being left under a temperature condition of preferably 5 to 70° C. or more preferably 15 to 45° C.

Any appropriate means can be selected as a melting means. Specific examples of the melting means include a water bath, an oil bath, and a thermostat bath.

When the gelled assembly is frozen and melted as described above, various bonds between the molecules or crystals of which the gel is formed are broken, and hence a sol is obtained. Although the gel can be turned into a sol by being subjected to an ultrasonic treatment for about 30 minutes as well, the various bonds between the molecules or crystals cannot be sufficiently broken, and hence the sol quickly gelates after irradiation with the ultrasonic wave. As a result, the mixing object cannot be uniformly dispersed in the sol. In contrast, the sol obtained by the freezing and the melting steps shows a significant reduction in its viscosity because the various bonds between the molecules or crystals are sufficiently broken. As a result, the sol can be uniformly mixed with the mixing object in the mixing step to be described later.

B-3. Mixing Step

Any appropriate substance can be selected as the mixing object depending on a purpose and the like. Specific examples of the mixing object include: vitamins; monosaccharides; disaccharides; oligosaccharides; polysaccharides such as hyaluronic acid, chitosan, and a cellulose that has been subjected to hydrophilic treatment; alcohols; polyols such as glycerin and propylene glycol; metal oxides such as zirconia and titanium oxide; dyes; physiologically active substances such as hormones, cytokines, hematopoietic factors, and growth factors; peptides; enzymes; antibodies; DNAs; RNAs; catalysts; crosslinking agents; culture solutions; and other general low-molecular-weight compounds. Alternatively, the mixing object may be a biological sample such as a cell, a cell colony, a tissue, a microorganism, or a virus. The cell may be an animal cell, or may be a plant cell. Examples of the microorganism include bacteria, yeasts, and protozoans. Only one kind of mixing object may be used, or two or more kinds of mixing objects may be used.

The amount in which the mixing object is mixed can be set to any appropriate amount as long as the sol can reconstitute the gelled assembly. In the case of, for example, the self-assembling peptide sol, a peptide concentration after the mixing is set to preferably 0.1 to 5 w/v % or more preferably 0.2 to 3 w/v %.

The mixing is performed during a time period for which the sol obtained in the above melting step maintains its sol state. In the case of, for example, the sol of the self-assembling peptide, the mixing can be suitably performed at preferably −2 to 15° C. or more preferably −2 to 5° C. because, in such temperature range, rapid gelation can be prevented and, as a result, a sufficient mixing time can be secured. It should be noted that the above temperature range is the temperature range of the peptide sol containing the mixing object, i.e., the peptide sol that is being mixed with the mixing object.

The mixing is preferably performed so that the molecules or crystals and the mixing object may be sufficiently dispersed in the sol. Neither a mixing time nor a mixing means is limited. Any appropriate means can be selected as the mixing means. In large-scale mixing, a stirring rod, a mixer, or the like can be used. Small-scale mixing may be performed by a manual operation such as pipetting.

Each of the freezing step, the melting step, and the mixing step described above may be repeatedly performed twice or more.

B-4. Gelling Step

Conditions for the reconstitution of the gel (such as a temperature and a time) are not limited as long as the gelled assembly is reconstituted, and the conditions can be appropriately set depending on, for example, the kinds and concentration of the molecules or crystals, and the kind of the medium. When the molecules in the sol are self-assembling molecules, the gel can be spontaneously reconstituted as a result of molecular-assembling by setting the conditions to appropriate ones.

For example, in the case where the self-assembling peptide gel is reconstituted, the sol into which the mixing object has been mixed obtained in the above mixing step has only to be left at rest. The temperature at which the sol is left at rest is preferably 15° C. or higher, or more preferably 25° C. or higher. The time period for which the sol is left at rest is preferably 1 minute or more, or more preferably 5 minutes or more. In addition, a place where the sol is left at rest is not limited, and examples of the place include the inside of a container made of glass, plastic, or the like, the inside of a cell culture instrument such as a dish, and the inside of a medical instrument such as a syringe. Further, the following is also permitted. That is, the sol into which the above mixing object has been mixed is injected into a living organism immediately after the mixing, and is caused to gel on the spot.

The mixing object can be present in the reconstituted gelled assembly in a state of being uniformly dispersed.

C. Production Method

According to another aspect of the present invention, there can be provided a method for producing a gelled assembly into which a mixing object has been mixed. The production method includes freezing the gelled assembly, melting the frozen assembly to obtain a sol, mixing the resultant sol and the mixing object, and reconstituting the gelled assembly from the sol into which the mixing object has been mixed. Each step is as described in the above section B. According to the production method, the gelled assembly into which the mixing object has been uniformly dispersed can be obtained.

EXAMPLES

Hereinafter, the present invention is described specifically by way of examples. However, the present invention is not limited by those examples.

Test Example 1

A self-assembling peptide 1 ([CH$_3$CO]-RLDLRLAL-RLDLR-[NH$_2$]) (SEQ ID NO:1) whose N-terminal was acetylated and whose C-terminal was amidated was obtained by an ordinary method. The self-assembling peptide 1 was dissolved in water, and an aqueous solution of NaHCO$_3$ was added to the solution so that its final concentration was 1.2 mM. A peptide concentration in the resultant peptide solution was 1 w/v %. The peptide solution was left at rest at room temperature for 10 minutes. As a result, a self-assembling peptide gel was obtained.

The resultant self-assembling peptide gel was frozen with liquid nitrogen. Next, the frozen self-assembling peptide gel was partially melted with warm water at 37° C., and then the resultant was left at rest at room temperature so as to be melted. As a result, a sol was obtained. 300 μl of the resultant sol was put into a container storing 200 μl of DMEM culture medium containing NIH3T3 cells at a concentration of 3.25×10$^5$ cells/ml, and the contents were mixed by performing pipetting three times. As a result, a sol into which the cells were mixed was obtained.

100 μl of each of the upper layer, middle layer, and lower layer of the resultant cell-mixed sol were sampled, and each sample was diluted with PBS five-fold. The number of cells at each position in the cell-mixed sol was determined with each of the diluted samples by measuring the number of cells in each of four divisions on a hematocytometer. Table 1 shows the results.

Test Example 2

As the self-assembling peptide gel, "BD™ PuraMatrix™ Peptide Hydrogel" (BD Biosciences Inc., peptide concentration: 1 w/v %, pH 3) was used.

The above self-assembling peptide gel was frozen with liquid nitrogen. Next, the frozen self-assembling peptide gel was partially melted with warm water at 37° C., and then the resultant was left at rest at room temperature so as to be melted. As a result, a sol was obtained. 300 μl of the resultant sol was put into a container storing 200 μl of DMEM culture medium containing NIH3T3 cells at a concentration of 5.38×10$^5$ cells/ml, and the contents were mixed by performing pipetting three times. As a result, a sol into which the cells were mixed was obtained.

The number of cells at each position in the resultant cell-mixed sol was determined in the same manner as in Test Example 1. Table 1 shows the results.

Comparative Test Example 1

A self-assembling peptide gel obtained in the same manner as in Test Example 1 was subjected to an ultrasonic treatment (product name "ULTRASONIC CLEANER US-4R" (manufactured by AS ONE Corporation, tank volume 9.5 L), 160 W, 30 minutes). As a result, a sol was obtained. 300 μl of the resultant sol was put into a container storing 200 μl of DMEM culture medium containing NIH3T3 cells at a concentration of 3.25×10$^5$ cells/ml, and the contents were mixed by performing pipetting three times. As a result, a sol into which the cells were mixed was obtained.

The number of cells at each position in the resultant cell-mixed sol was determined in the same manner as in Test Example 1. Table 1 shows the results.

Comparative Test Example 2

The same self-assembling peptide gel used in Test Example 2 was subjected to an ultrasonic treatment (product name "ULTRASONIC CLEANER US-4R" (manufactured by AS ONE Corporation, tank volume 9.5 L), 160 W, 30 minutes). As a result, a sol was obtained. 300 μl of the resultant sol was put into a container storing 200 μl of DMEM culture medium containing NIH3T3 cells at a concentration of 5.38×10$^5$ cells/ml, and the contents were mixed by performing pipetting three times. As a result, a sol into which the cells were mixed was obtained.

The number of cells at each position in the resultant cell-mixed sol was determined in the same manner as in Test Example 1. Table 1 shows the results.

TABLE 1

| Sampling position | Test Example 1 | Comparative Test Example 1 | Test Example 2 | Comparative Test Example 2 |
|---|---|---|---|---|
| Upper layer | 1.45 | 1.18 | 2.28 | 2.45 |
| Middle layer | 1.35 | 1.33 | 2.08 | 0.65 |
| Lower layer | 1.12 | 0.35 | 2.13 | 2.25 |
| Theoretical value | 1.3 | | 2.15 | |

(unit: 10$^5$ cells/ml)

As shown in Table 1, the mixing object can be dispersed in a sol obtained by the freezing and the melting steps more uniformly than in a sol obtained by the ultrasonic treatment.

Example 1

The above self-assembling peptide 1 was dissolved in water, and an aqueous solution of NaHCO$_3$ was added to the solution so that its final concentration was 1.2 mM. The peptide concentration in the resultant peptide solution was 0.8 w/v %. The peptide solution was left at rest at room temperature for 10 minutes. As a result, a self-assembling peptide gel was obtained.

The resultant self-assembling peptide gel was frozen with liquid nitrogen. Next, the frozen self-assembling peptide gel was partially melted with warm water at 37° C., and then the resultant was left at rest at room temperature so as to be melted. As a result, a sol was obtained. 300 μL of the resultant sol was transferred to a sampling tube, and 450 μL of DMEM culture medium containing phenol red was added to the sol. Then, the mixing by pipetting was performed five times.

Figure 1A:
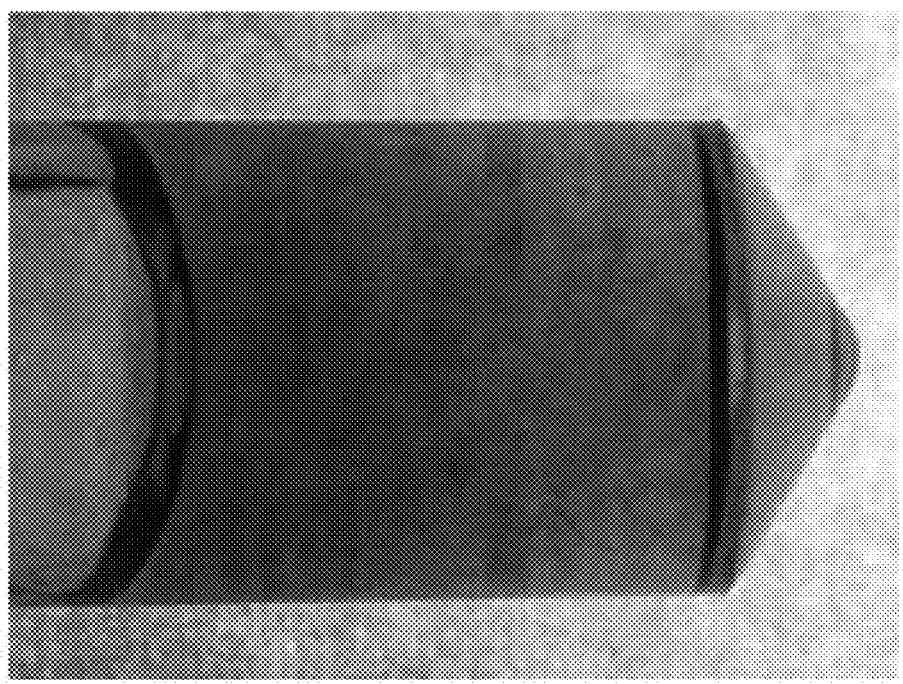

Next, the sampling tube was left at rest at 25° C. for 5 minutes. As a result, a self-assembling peptide gel was reconstituted. FIG. 1A shows the photograph of the reconstituted gel.

Example 2

As the self-assembling peptide gel, "BD™ PuraMatrix™ Peptide Hydrogel" (BD Biosciences Inc., peptide concentration: 1 w/v %, pH 3) was used.

The above self-assembling peptide gel was frozen with liquid nitrogen. Next, the frozen self-assembling peptide gel was partially melted with warm water at 37° C., and then the resultant was left at rest at room temperature so as to be melted. As a result, a sol was obtained. 300 μL of the resultant sol was transferred to a sampling tube, and 450 μL of an aqueous solution of eosin was added to the sol. Then, the mixing by pipetting was performed five times.

Figure 2B:
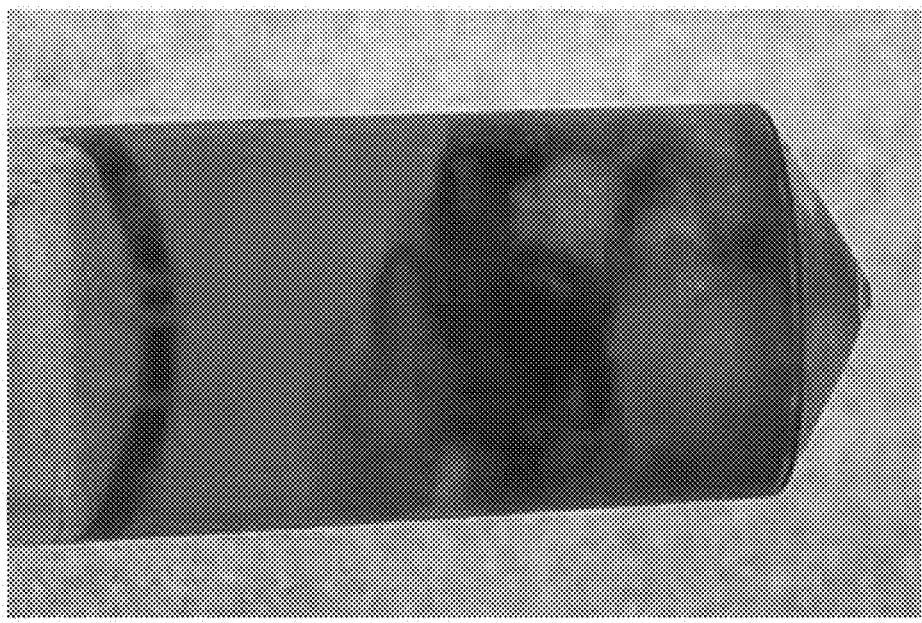
FIG. 2A is a photograph of a gel reconstituted in Example 2 and FIG. 2B is a photograph of a gel reconstituted in Comparative Example 2.
Figure 2A:
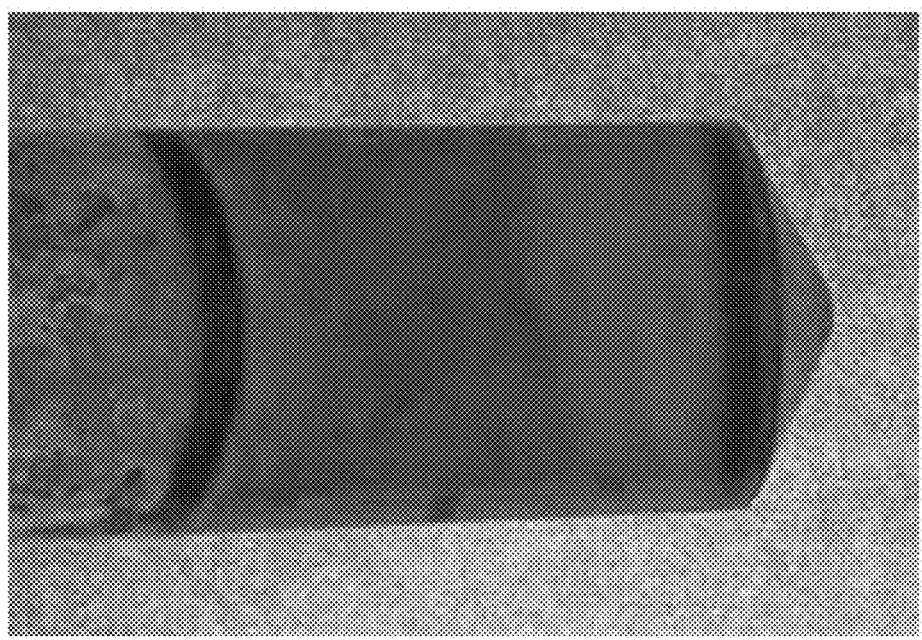

Next, the sampling tube was left at rest at 25° C. for 20 minutes. As a result, a self-assembling peptide gel was reconstituted. FIG. 2A shows the photograph of the reconstituted gel.

Example 3

Figure 3B:
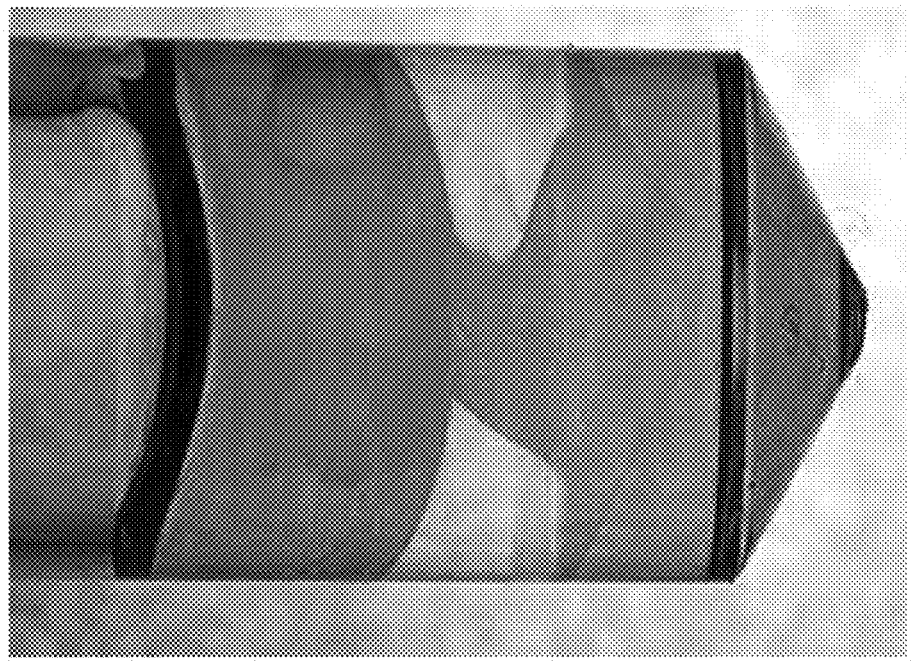
FIG. 3A is a photograph of a gel reconstituted in Example 3 and FIG. 3B is a photograph of a gel reconstituted in Comparative Example 3.
Figure 3A:
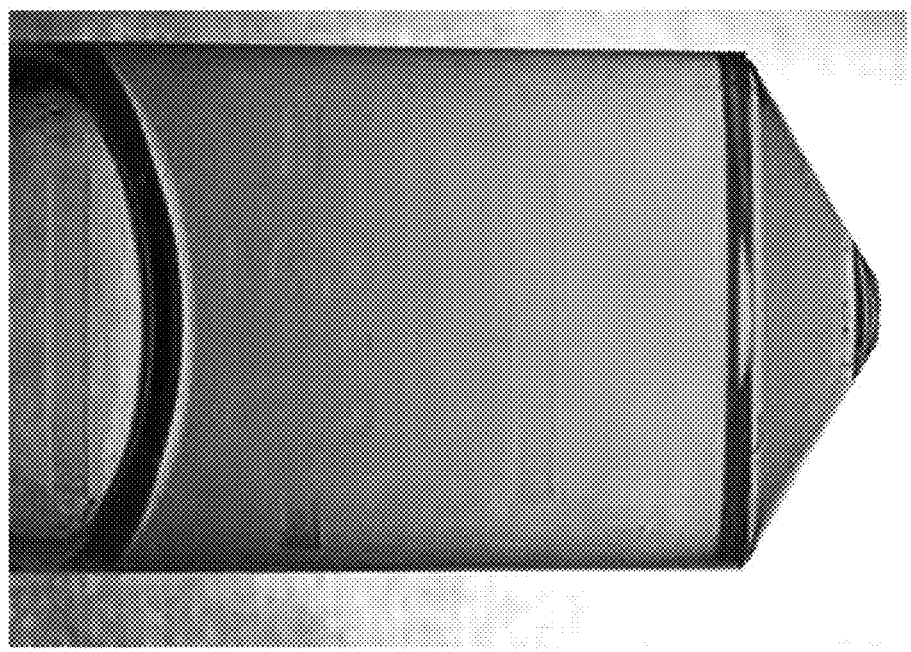

A self-assembling peptide gel was reconstituted in the same manner as in Example 1 except that a 50 μM aqueous solution of FITC-labeled insulin was mixed instead of the DMEM culture medium containing phenol red. FIG. 3A shows the photograph of the reconstituted gel.

Example 4

Figure 4B:
FIG. 4A is a photograph of a gel reconstituted in Example 4 and FIG. 4B is a photograph of a gel reconstituted in Comparative Example 4.
Figure 4A:
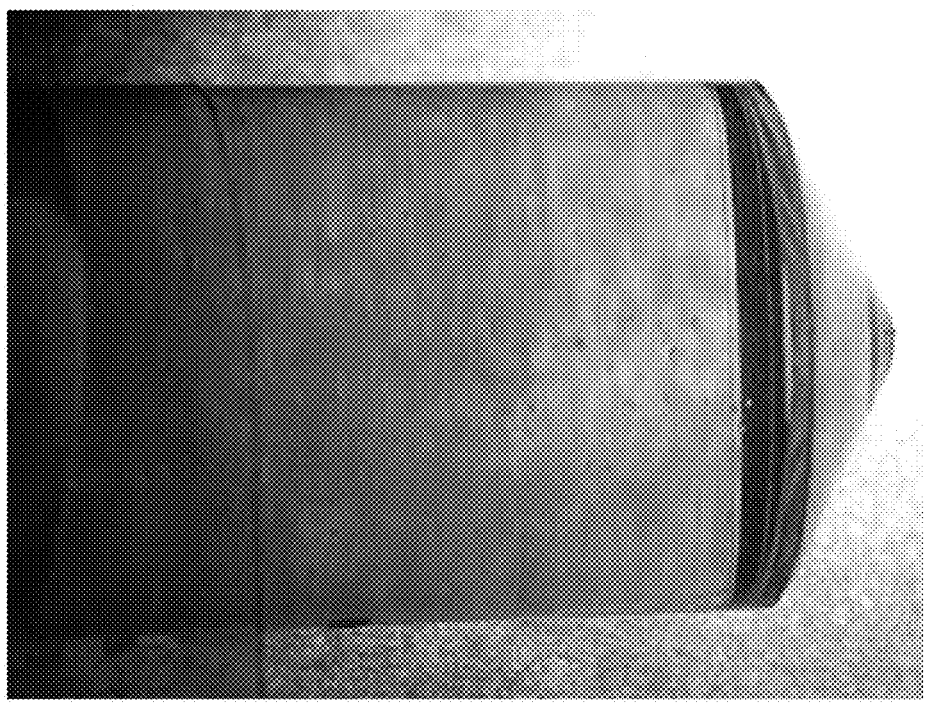

A self-assembling peptide gel was reconstituted in the same manner as in Example 2 except that a 50 μM aqueous solution of FITC-labeled insulin was mixed instead of the aqueous solution of eosin. FIG. 4A shows the photograph of the reconstituted gel.

Comparative Example 1

A self-assembling peptide gel was reconstituted in the same manner as in Example 1 except that a sol was obtained by performing an ultrasonic treatment (product name "ULTRASONIC CLEANER US-4R" (manufactured by AS ONE Corporation, tank volume 9.5 L), 160 W, 30 minutes) instead of the freezing and the melting steps. FIG. 1B shows the photograph of the reconstituted gel.

Comparative Example 2

A self-assembling peptide gel was reconstituted in the same manner as in Example 2 except that a sol was obtained by performing an ultrasonic treatment (product name "ULTRASONIC CLEANER US-4R" (manufactured by AS ONE Corporation, tank volume 9.5 L), 160 W, 30 minutes) instead of the freezing and the melting steps. FIG. 2B shows the photograph of the reconstituted gel.

Comparative Example 3

A self-assembling peptide gel was reconstituted in the same manner as in Example 3 except that a sol was obtained by performing an ultrasonic treatment (product name "ULTRASONIC CLEANER US-4R" (manufactured by AS ONE Corporation, tank volume 9.5 L), 160 W, 30 minutes) instead of the freezing and the melting steps. FIG. 3B shows the photograph of the reconstituted gel.

Comparative Example 4

A self-assembling peptide gel was reconstituted in the same manner as in Example 4 except that a sol was obtained by performing an ultrasonic treatment (product name "ULTRASONIC CLEANER US-4R" (manufactured by AS ONE Corporation, tank volume 9.5 L), 160 W, 30 minutes) instead of the freezing and the melting steps. FIG. 4B shows the photograph of the reconstituted gel.

As illustrated in FIGS. 1A and 1B to 4A and 4B, according to the method of the present invention, the mixing object can be uniformly dispersed within a short time period by subjecting a gelled molecular-assembly to the freezing and the melting treatment to turn the assembly into a sol. On the other hand, when the sol obtained by the ultrasonic treatment is used, the reconstituted gel hazes, and thus it can be found that the mixing object was nonuniformly dispersed.

Reference Example 1

A gelled assembly containing a trade name "Laponite XLG" (manufactured by Laporte-Ind. Ltd.) at a concentration of 6 w/v % (medium: water) was frozen with liquid nitrogen. Next, the frozen assembly was partially melted with warm water at 37° C., and then the resultant was left at rest at room temperature so as to be melted. As a result, a sol was obtained. The resultant sol was left at rest at 25° C. for 5 hours. As a result, a gelled assembly was reconstituted.

Reference Example 2

A gelled assembly containing a trade name "Laponite XLG" (manufactured by Laporte-Ind. Ltd.) at a concentration of 2 w/v % (medium: an aqueous solution containing 0.75 wt % of a surfactant (trade name "OS-14" manufactured by Nikko Chemicals Co., Ltd.) and 1.0 wt % of EDTA-2Na) was frozen with liquid nitrogen. Next, the frozen assembly was partially melted with warm water at 37° C., and then the resultant was left at rest at room temperature so as to be melted. As a result, a sol was obtained. The resultant sol was left at rest at 25° C. for 15 minutes. As a result, a gelled assembly was reconstituted.

The mixing method and production method of the present invention are suitably applicable to regenerative medicine, or the production or use of, for example, a drug delivery system, cosmetics, a synthetic vitreous, a hemostatic drug, an injection for cosmetic surgery, a bone filler, a joint lubricant, or a water retention material for humectation.

[Sequence Listing Free Text]

SEQ ID NO: 1 represents a self-assembling peptide which may be used in the present invention.

SEQ ID NO: 2 represents a self-assembling peptide which may be used in the present invention.

SEQ ID NO: 3 represents a self-assembling peptide which may be used in the present invention.

Many other modifications will be apparent to and be readily practiced by those skilled in the art without departing from the scope and spirit of the invention. It should therefore be understood that the scope of the appended claims is not intended to be limited by the details of the description but should rather be broadly construed.

What is claimed is:

1. A method for mixing a mixing object into a gelled assembly, the method comprising:
   freezing the gelled assembly;
   melting the frozen assembly to obtain a sol;
   mixing the resultant sol and the mixing object; and
   reconstituting the gelled assembly from the sol into which the mixing object has been mixed.

2. A method according to claim 1, wherein the gelled assembly comprises a gel formed by molecular-assembling of self-assembling molecules.

3. A method according to claim 1, wherein the gelled assembly comprises a gel formed by assembling of clay mineral crystals.

4. A method according to claim 2, wherein the self-assembling molecules comprise self-assembling peptides.

5. A method for producing a gelled assembly into which a mixing object has been mixed, the method comprising:
   freezing the gelled assembly;
   melting the frozen assembly to obtain a sol;
   mixing the resultant sol and the mixing object; and
   reconstituting the gelled assembly from the sol into which the mixing object has been mixed, wherein the reconstituting step comprises resting the sol for 1 minute or more.

* * * * *

SEQUENCE LISTING

```
<160> NUMBER OF SEQ ID NOS: 3

<210> SEQ ID NO 1
<211> LENGTH: 13
<212> TYPE: PRT
<213> ORGANISM: Artificial
<220> FEATURE:
<223> OTHER INFORMATION: self-assembling peptide

<400> SEQUENCE: 1

Arg Leu Asp Leu Arg Leu Ala Leu Arg Leu Asp Leu Arg
1               5                   10

<210> SEQ ID NO 2
<211> LENGTH: 13
<212> TYPE: PRT
<213> ORGANISM: Artificial
<220> FEATURE:
<223> OTHER INFORMATION: self-assembling peptide

<400> SEQUENCE: 2

Arg Leu Asp Leu Arg Leu Leu Leu Arg Leu Asp Leu Arg
1               5                   10

<210> SEQ ID NO 3
<211> LENGTH: 14
<212> TYPE: PRT
<213> ORGANISM: Artificial
<220> FEATURE:
<223> OTHER INFORMATION: self-assembling peptide

<400> SEQUENCE: 3

Arg Leu Asp Leu Arg Leu Ala Leu Arg Leu Asp Leu Arg Leu
1               5                   10
```